United States Patent
Amendola et al.

(10) Patent No.: US 8,790,347 B2
(45) Date of Patent: Jul. 29, 2014

(54) TIBIAL RASP

(75) Inventors: Annunziato Amendola, Coralville, IA (US); Jacob A. Jolly, Naples, FL (US); Gary Scott Sherman, Naples, FL (US)

(73) Assignee: Arthrex, Inc., Naples, FL (US)

( * ) Notice: Subject to any disclaimer, the term of this patent is extended or adjusted under 35 U.S.C. 154(b) by 580 days.

(21) Appl. No.: 12/825,152

(22) Filed: Jun. 28, 2010

(65) Prior Publication Data
US 2011/0004216 A1     Jan. 6, 2011

Related U.S. Application Data

(60) Provisional application No. 61/222,747, filed on Jul. 2, 2009.

(51) Int. Cl.
*A61B 17/16* (2006.01)

(52) U.S. Cl.
USPC .............................. 606/85; 606/79

(58) Field of Classification Search
CPC ............... A61B 17/320016; A61B 17/32002; A61B 17/1659; A61B 17/1675; A61B 17/1677; A61B 17/1662; A61F 2/46; A61F 2/464404
USPC .......... 606/79–86 R; 433/141–145, 165–166; 623/13.11–13.2, 19.11
See application file for complete search history.

(56) References Cited

U.S. PATENT DOCUMENTS

| | | | |
|---|---|---|---|
| 4,511,334 A * | 4/1985 | Grafelmann | 433/165 |
| 5,630,819 A * | 5/1997 | Ashby et al. | 606/81 |
| 5,879,353 A * | 3/1999 | Terry | 606/85 |
| 6,676,706 B1 * | 1/2004 | Mears et al. | 623/22.4 |
| 2007/0010822 A1 * | 1/2007 | Zalenski et al. | 606/79 |
| 2007/0038302 A1 * | 2/2007 | Shultz et al. | 623/19.11 |
| 2007/0233128 A1 | 10/2007 | Schmieding et al. | |
| 2007/0233131 A1 * | 10/2007 | Song et al. | 606/79 |
| 2007/0265632 A1 * | 11/2007 | Scifert et al. | 606/82 |
| 2008/0039852 A1 | 2/2008 | Schmieding et al. | |
| 2008/0114366 A1 * | 5/2008 | Smucker et al. | 606/88 |
| 2008/0275512 A1 | 11/2008 | Albertorio et al. | |
| 2011/0213371 A1 * | 9/2011 | Anthony et al. | 606/85 |

FOREIGN PATENT DOCUMENTS

| | | | | |
|---|---|---|---|---|
| WO | WO 01/66021 A1 | 9/2001 | | |
| WO | WO 2006/004885 A2 | 1/2006 | | |
| WO | WO 2008/154491 A1 | 12/2008 | | |
| WO | WO 2009146026 A1 * | 12/2009 | | A61B 17/17 |

* cited by examiner

*Primary Examiner* — Todd Manahan
*Assistant Examiner* — Marcela I Shirsat
(74) *Attorney, Agent, or Firm* — Dickstein Shapiro LLP

(57) ABSTRACT

Methods and apparatus for arthroscopically-assisted preparation of the tibia to accept an unicompartmental implant that includes the step of removing bone from the tibial plateau to correct depth, diameter and proper angle by employing a tibial rasp comprising a cutter with a plurality of teeth on the bottom surface and a side surface (for example, the front side). The tibial rasp may be used in conjunction with an additional starter rasp that can cut only in one direction (for example, cutting to establish only the depth of the tunnel or socket).

10 Claims, 4 Drawing Sheets

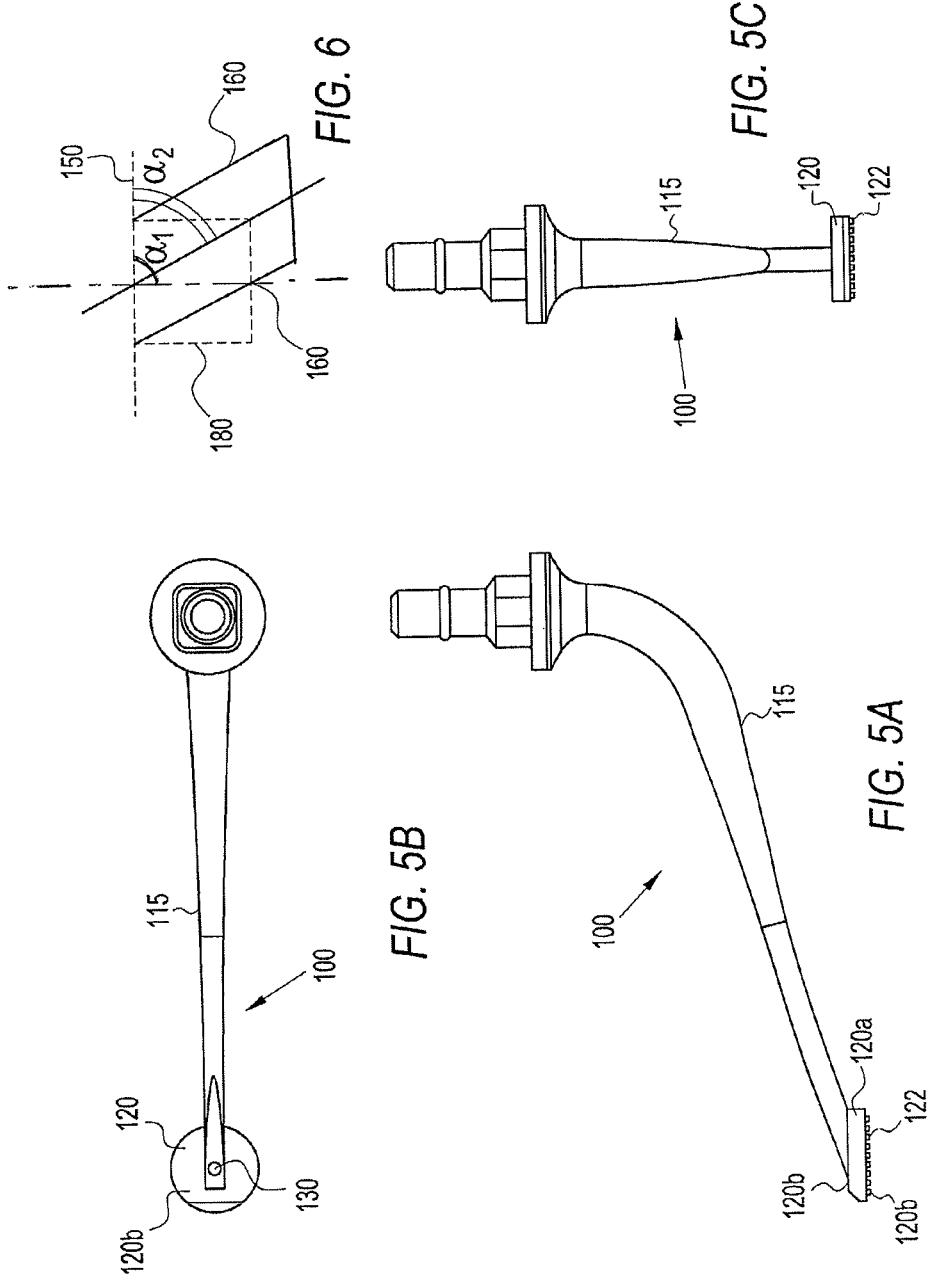

TIBIAL RASP

CROSS-REFERENCE TO RELATED APPLICATIONS

This application claims the benefit of U.S. Provisional Application Ser. No. 61/222,747, filed Jul. 2, 2009, the entire disclosure of which is incorporated by reference herein.

FIELD OF THE INVENTION

The present invention relates to the field of arthroscopic surgery and, more particularly, to improved instrumentation for reconstructive knee surgery.

BACKGROUND OF THE INVENTION

Partial knee replacement surgery (also called unicompartmental knee arthroplasty) is known in the art for the treatment of osteoarthritis of the knee joint. During partial knee replacement surgery, the bone and cartilage on the end of the femur and top of the tibia are removed. A knee replacement implant made of various biocompatible materials such as metal or plastic is then placed to function as a new knee joint. Depending on the condition of the cartilage on the undersurface of the kneecap, the cartilage may also be replaced. The knee replacement implant typically comprises (i) a femoral component which fits on the femur, (ii) a tibial component which fits on the tibia, and optionally (iii) a patellar component, made of plastic and which replaces the cartilage on the undersurface of the kneecap, and optionally (iv) a plastic insert which fits between the femoral and tibial components.

Placement of the knee replacement implant typically involves the steps of: (i) forming a tibial socket in the tibial plateau; (ii) performing at least one cut on the femoral condyle; and (iii) placing implants or components into the socket on the tibial plateau and into the cut in the femur. These steps are performed using precise instruments to create exact surfaces to accommodate the implant. For example, instrumentation and apparatus for arthroscopic unicompartmental knee surgery (which include a femoral component and a tibial component) are described for example in U.S. Patent Application Publication No. 2008/0275512, the disclosure of which is incorporated by reference. U.S. Patent Application Publication No. 2008/0039852 (the disclosure of which is also incorporated by reference) describes the use of a dual-sided cutter for forming the femoral trough and tibial socket by retrograde drilling.

SUMMARY OF THE INVENTION

The present invention provides techniques and apparatus for unicompartmental knee surgery by utilizing novel tibial rasps (a starter tibial rasp and a second tibial rasp) that allow the surgeon and/or medical personnel to rasp away bone at the tibial plateau to the proper diameter, depth and angle (in a direction about normal to the tibial plateau) to facilitate placement of the tibial implant.

The starter tibial rasp of the present invention is provided with a cutter (a first rasping body) designed to cut a tibial socket to a set depth using a guide pin that has been inserted in previous steps of retrodrilling a tunnel through the tibia as described in U.S. Patent Application Publication No. 2007/0233128, the disclosure of which is incorporated in its entirety by reference herein. The cutter of the starter tibial rasp is provided with a plurality of teeth located on the bottom surface of the cutter. The cutter is also cannulated to fit over the guide pin located in the tibial tunnel. The guide pin prevents the rasp from cutting outside the desired diameter of the tibial socket. The rasp can only cut establishing a depth of the socket. This rasp is used to start a socket and then a second tibial rasp (described below) is used to complete to formation of the tibial socket. The guide pin is removed prior to using the second tibial rasp. Removal of the pin allows the second rasp to self adjust to approximately normal to the tibial plateau.

The second tibial rasp of the present invention is provided with a cutter (a second rasping body) designed to enlarge (to cut) a tibial socket to a set depth, diameter and proper angle (about perpendicular to the tibial plateau) so that the tibial implant will seat easily and properly in the prepared socket. The cutter of the second tibial rasp is provided with a plurality of teeth located on the bottom of the cutter and along only one side of the cutter (for example, the front side). In this manner, the cutter is used to rasp away bone until the top of the cutter portion of the instrument is flush with the tibial plateau, guaranteeing the depth and angle of the cut. The cutter of the second tibial rasp may be provided in various diameters to match various implant sizes.

By utilizing the tibial rasps of the present invention in lieu of a typical cutting instrument, the surgeon can position the instruments close to perpendicular to the tibial plateau (when introducing the instrument from the top of the plateau) and more easily visualize and correctly create the tibial socket (for insertion of the tibial implant during the unicompartmental knee surgery).

The present invention also provides a method of arthroscopically-assisted preparation of the tibia to accept a unicompartmental implant that includes the steps of: (i) removing bone from the tibial plateau by employing a first starter tibial rasp comprising a cannulated cutter with a plurality of teeth provided only on one side of the cutter (for example, only on the bottom of the cutter); and optionally (ii) removing additional bone to correct depth, diameter and proper angle by employing a second tibial rasp comprising a cutter with a plurality of teeth on the bottom surface and a side surface (for example, the front side).

The present invention also provides a method of arthroscopically-assisted preparation of the tibia to accept an unicompartmental implant that includes the step of removing bone from the tibial plateau to correct depth, diameter and proper angle by employing only one tibial rasp comprising a cutter with a plurality of teeth on the bottom surface and a side surface (for example, the front side).

Other features and advantages of the present invention will become apparent from the following description of the invention which refers to the accompanying drawings.

BRIEF DESCRIPTION OF THE DRAWINGS

FIGS. 5A-C illustrate various views of the starter tibial rasp of FIG. 4; and

FIG. 6 illustrates the tibial socket created by the tibial rasps of FIGS. 1 and 4.

DETAILED DESCRIPTION OF THE INVENTION

Figure 2:
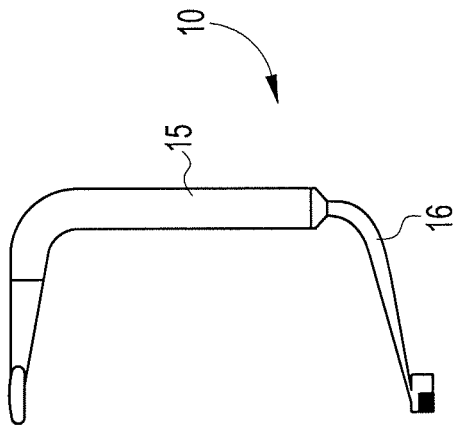
FIG. 2 illustrates an expanded view of the tibial rasp of FIG. 1.
Figure 1:
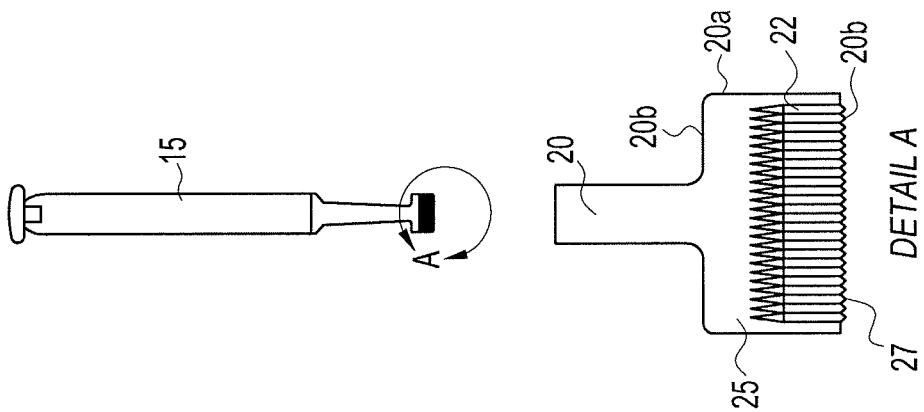
FIG. 1 illustrates a perspective view of a tibial rasp of the present invention.
Figure 1:
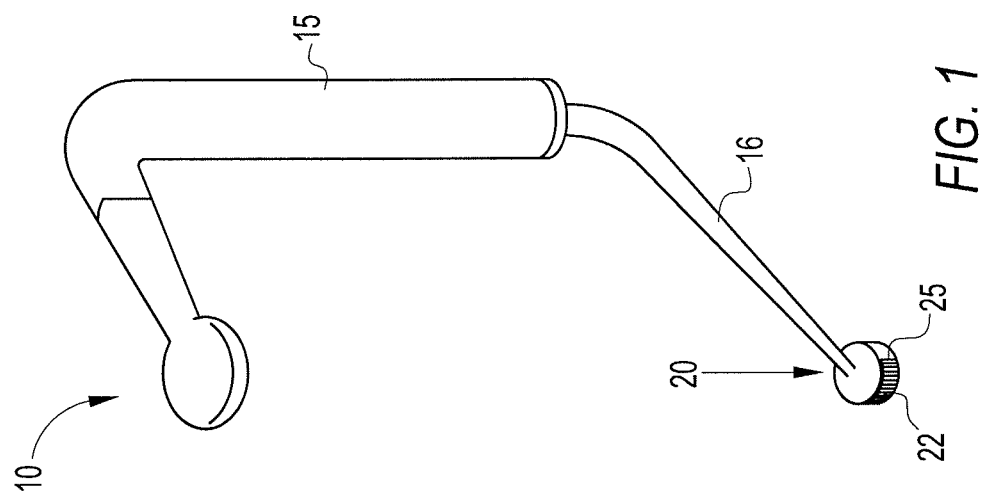
Figure 3:
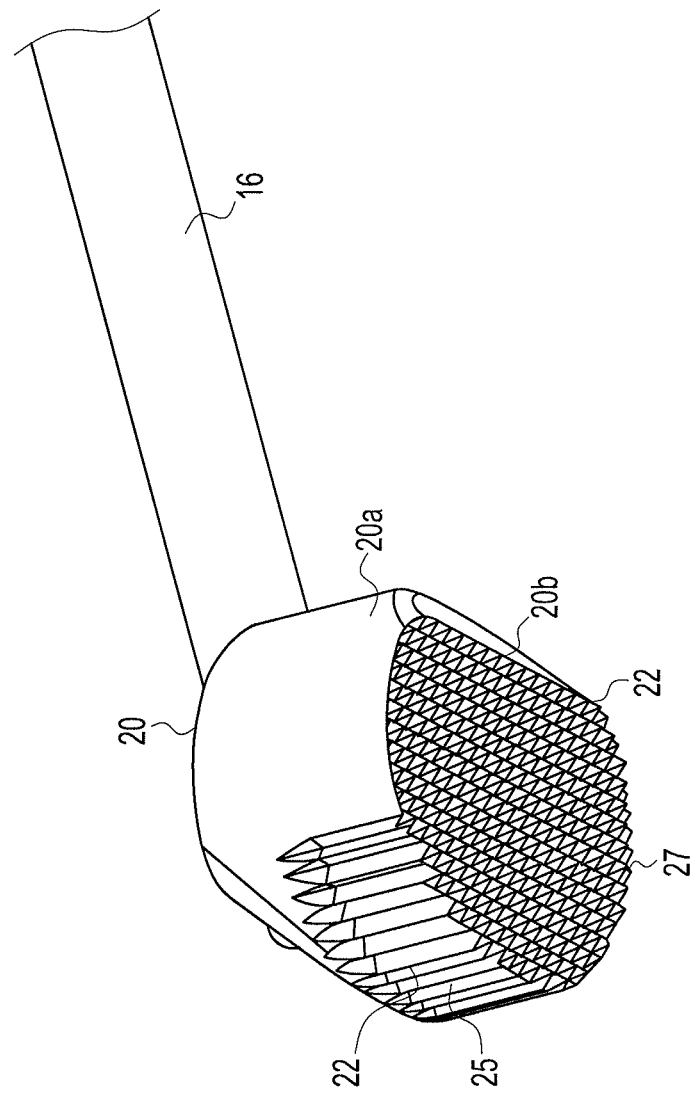
FIG. 3 illustrates a close-up view of the cutter of the tibial rasp of FIG. 1.
Figure 4:
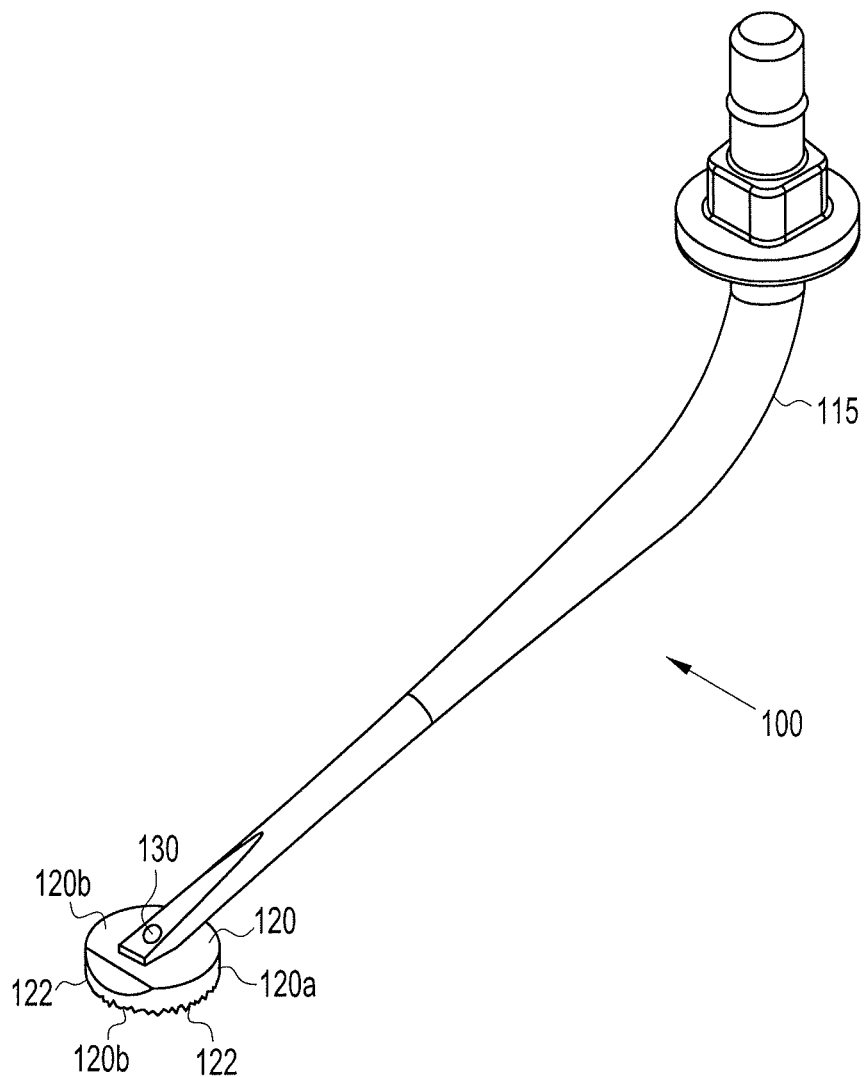
FIG. 4 illustrates a perspective view of a starter tibial rasp of the present invention.

Referring now to the drawings, where like elements are designated by like reference numerals, FIGS. 4 and 5 illustrate various views of a starter tibial rasp 100 (a first tibial rasp 100) of the present invention, while FIGS. 1-3 illustrate details of a second tibial rasp 10 of the present invention. The first and second raps 100, 10 of the present invention may be provided as an assembly, pre-packaged before surgery and ready for use, or may be assembled during the surgery by medical personnel.

The starter tibial rasp 100 of the present invention is provided with a handle 115 and a cutter 120 (rasping body 120) designed to create a bone socket or tunnel. Cutter 120 has a generally cylindrical configuration and is provided with an outer cylindrical surface 120a and opposing surfaces 120b. The cutter 120 is cannulated (provided with a hole 130 through it) for placement over a guide pin secured in the tibia by retrograde drilling. The cutter 120 has a plurality of teeth 122 on bottom surface 120b (for example, the bottom surface of the two opposing surfaces 120b) for creating the socket or tunnel.

The second tibial rasp 10 of the present invention is provided with a handle 15 attached to a shaft 16 and a cutter 20 (rasping body 20) designed to enlarge (to cut) the tibial tunnel or socket created with the starter tibial rasp 100 to a set depth, diameter and proper angle (about perpendicular to the tibial plateau) so that the tibial implant will seat easily and properly in the prepared tunnel. Preferably, cutter 20 is releasably attached to shaft 16. Cutter 20 has preferably a general cylindrical configuration, with an outer cylindrical side or surface 20a and two opposing sides or surfaces 20b (FIG. 2).

The cutter 20 of the tibial rasp 10 is provided with a plurality of teeth 22 located only on a portion of outer cylindrical surface 20a. In an exemplary embodiment, cutter 20 is provided with a plurality of teeth 22 on one side of the cutter (for example, only on the front side 25 of surface 20a). A second plurality of teeth 27 is provided on one of the other two opposing surfaces 20b (for example, on the bottom side or surface 20b) of the cutter 20. In this manner, the cutter 20 is used to rasp away bone until the top of the cutter 20 is flush with the tibial plateau, guaranteeing the depth of the cut. The cutter 20 of the tibial rasp 10 may be provided in various diameters to match various implant sizes.

Tibial rasp 10 of the present invention allows the surgeon and/or medical personnel to rasp away bone at the tibial plateau to the proper diameter, depth and angle (in a direction about normal to the tibial plateau) to facilitate placement of the tibial implant.

By utilizing the starter tibial rasp 100 of the present invention in lieu of a typical cutting instrument used in the art, the surgeon can position the instrument perpendicular to the tibial plateau (when introducing the instrument from the top of the plateau over the guide pin) and more easily create a socket having the correct orientation for further insertion of the tibial implant during the unicompartmental knee surgery. The second tibial rasp 10 follows the starter rasp and removes the additional bone not only for the proper depth of the socket but also for the proper orientation of the socket.

FIG. 6 illustrates the tibial tunnel 160 created from the retrograde drilling step which is at an angle α2 of 45° also referred to as the parallax error. The proper orientation of the tibial socket for placement of the tibial implant is about perpendicular to the tibial plateau (angle α1 of 90°). The plurality of teeth 22 along the front side 25 of the second tibial rasp 10 removes the area of bone depicted as dotted lines 180 in FIG. 6, to create the socket with the desired orientation (i.e., at angle α1 relative to surface 150 of the bone).

In an exemplary embodiment only, cutters 20, 120 are detachable from the handle 15 of the tibial rasp 10. In this manner, an additional instrument (for example, an impactor) may be attached to handle 15 in lieu of the cutter so that the instrument (i.e., the impactor) may be employed to drive in the tibial implant, for example, subsequent to the step of enlarging the tibial socket.

Although the present invention has been described in connection to a tibial rasp used for removing bone from a tibial socket, the invention is not limited to this exemplary only embodiment, and contemplates an instrument employed for enlarging any socket or tunnel formed into a bone (for example, a hip replacement rasp, among others).

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of arthroscopically-assisted preparation of a bone to accept an implant, the method comprising the steps of:
   introducing a first arthroscopic cylindrical rasp through an arthroscopic portal and into a joint and removing bone to form a first tunnel or socket having a first depth, a first diameter, and a first longitudinal axis forming a first angle with a surface of the bone;
   replacing the first arthroscopic cylindrical rasp with a second arthroscopic cylindrical rasp, the second arthroscopic cylindrical rasp being provided with a cutter having an outer cylindrical surface and two opposing surfaces, wherein one of the two opposing surfaces is provided with a first plurality of teeth and wherein only a portion of the outer cylindrical surface is provided with a second plurality of teeth; and
   introducing the arthroscopic cylindrical rasp through the arthroscopic portal and into the joint and removing bone from the first tunnel or socket with the second cylindrical rasp to enlarge the first tunnel or socket to form a second tunnel or socket having a second depth, a second diameter, and a second longitudinal axis forming a second angle with the surface of the bone, wherein the second depth is greater than the first depth and the second diameter is greater than the first diameter, wherein the first arthroscopic cylindrical rasp cuts in one direction and the second arthroscopic cylindrical rasp cuts in an axial and a rotational directions.

2. The method of claim 1, wherein the first arthroscopic rasp is provided with a cutter having an outer cylindrical surface and two opposing surfaces, wherein one of the two opposing surfaces is provided with a first plurality of teeth.

3. The method of claim 1, wherein about half of the outer cylindrical surface of the cutter of the second arthroscopic rasp is provided with the second plurality of teeth.

4. The method of claim 1, wherein the second angle is different from the first angle.

5. The method of claim 1, wherein the second angle is 90 degrees, and wherein the first angle is different from the second angle.

6. The method of claim 1, wherein the bone is tibia and wherein the first angle is 45 degrees and wherein the second angle is 90 degrees.

7. A method of preparing a tunnel or socket in tibia for accepting a tibial implant, the method comprising the steps of:
   providing an arthroscopic rasping instrument having a shaft and a first cylindrical cutter;
   inserting the first cylindrical cutter over a guide pin;

removing bone with the first cylindrical cutter to form a first tunnel or socket having a first depth, a first diameter, and a first longitudinal axis forming a first angle with a surface of the tibia;

removing the first cylindrical cutter from the shaft and removing the guide pin;

attaching a second cylindrical cutter to the shaft, the second cylindrical cutter having an outer cylindrical surface and two opposing surfaces, wherein one of the two opposing surfaces is provided with a first plurality of teeth and wherein only a portion of the outer cylindrical surface is provided with a second plurality of teeth; and introducing the second cylindrical cutter through an arthroscopic portal and into knee joint and removing bone from the first tunnel or socket with the second cylindrical cutter to enlarge the first tunnel or socket to form a second tunnel or socket having a second depth, a second diameter, and a second longitudinal axis forming a second angle with the surface of the tibia, wherein the first cylindrical cutter cuts in one direction and the second cylindrical cutter cuts in an axial and a rotational directions.

8. The method of claim 7, wherein the first cutter is provided with an outer cylindrical surface and two opposing surfaces, wherein one of the two opposing surfaces is provided with a first plurality of teeth.

9. The method of claim 7, wherein about half of the outer cylindrical surface of the second cylindrical cutter is provided with the second plurality of teeth.

10. The method of claim 7, wherein the first angle is 45 degrees and wherein the second angle is 90 degrees.

* * * * *